US006951411B1

(12) United States Patent
Kumar et al.

(10) Patent No.: US 6,951,411 B1
(45) Date of Patent: Oct. 4, 2005

(54) LIGHT BEAM GENERATION, AND FOCUSING AND REDIRECTING DEVICE

(75) Inventors: Krishna S. Kumar, Duluth, GA (US); Danny F. Lincoln, Commerce, GA (US); Jonathan A. Eppstein, Atlanta, GA (US); Michael R. Hatch, Sugar Hill, GA (US)

(73) Assignees: SpectRx, Inc., Norcross, GA (US); Altea Technologies, Inc., Tucker, GA (US)

( * ) Notice: Subject to any disclaimer, the term of this patent is extended or adjusted under 35 U.S.C. 154(b) by 74 days.

(21) Appl. No.: 10/018,913

(22) PCT Filed: Jun. 15, 2000

(86) PCT No.: PCT/US00/16576

§ 371 (c)(1),
(2), (4) Date: May 6, 2002

(87) PCT Pub. No.: WO00/78242

PCT Pub. Date: Dec. 28, 2000

Related U.S. Application Data (60) Provisional application No. 60/165,814, filed on Nov. 16, 1999, provisional application No. 60/140,003, filed on Jun. 18, 1999.

(51) Int. Cl.[7] .......................................... F21V 14/06
(52) U.S. Cl. .................. 362/284; 362/259; 362/282; 362/294; 606/17; 372/24; 359/211

(58) Field of Search ................. 362/109, 116, 119, 362/120, 157, 184, 185, 187, 197, 227, 232, 362/235, 236, 237, 244, 257, 259, 277, 202, 362/284, 294, 296, 282, 268, 269, 271, 272; 606/1, 2, 10, 13, 17, 27, 32–34, 167, 3, 11, 606/37, 39, 40; 359/196, 197, 198, 209, 211, 359/212, 216, 223, 226, 831; 372/9, 24

(56) References Cited

U.S. PATENT DOCUMENTS 3,657,792 A * 4/1972 Hug et al. .................. 359/218
3,699,474 A * 10/1972 Landry ........................ 372/17
3,866,032 A * 2/1975 Veres .......................... 362/259

(Continued)

FOREIGN PATENT DOCUMENTS

WO        WO 94/01904 A        1/1994

(Continued)

*Primary Examiner*—Thomas M. Sember
*Assistant Examiner*—Ismael Negron
(74) *Attorney, Agent, or Firm*—Altera Law Group, LLC (57) ABSTRACT

An improved light beam generation and focusing device (15, 50) has a light source (16, 51) constructed and arranged to emit at least one beam of light (20), and a lens assembly (17, 19, 56) constructed and arranged to focus the at least one beam of light on a surface plane. The device is constructed and arranged to sequentially direct the at least one beam of light to at least two spaced locations (21, 21') on the surface plane. The lens assembly comprises a collimating lens (17), and a spaced focusing lens (19).

17 Claims, 7 Drawing Sheets

U.S. PATENT DOCUMENTS

| | | | |
|---|---|---|---|
| 3,881,802 A * | 5/1975 | Helava | 359/211 |
| 4,079,230 A * | 3/1978 | Miyauchi et al. | 219/121.8 |
| 4,227,776 A * | 10/1980 | Morton et al. | 362/259 |
| 4,233,567 A * | 11/1980 | Chernoch | 372/34 |
| 4,393,393 A * | 7/1983 | Allen, Jr. et al. | 372/36 |
| 4,544,228 A * | 10/1985 | Rando | 359/211 |
| 4,573,067 A * | 2/1986 | Tuckerman et al. | 257/713 |
| 4,826,269 A | 5/1989 | Streifer et al. | |
| 4,881,233 A * | 11/1989 | von Arb et al. | 372/35 |
| 5,125,922 A * | 6/1992 | Dwyer et al. | 606/3 |
| 5,437,658 A | 8/1995 | Muller et al. | |
| 5,576,901 A * | 11/1996 | Hanchett | 359/877 |
| 5,586,981 A | 12/1996 | Hu | |
| 5,643,252 A | 7/1997 | Waner et al. | |
| 5,790,584 A * | 8/1998 | Kong et al. | 372/9 |
| 5,839,446 A * | 11/1998 | Waner et al. | 606/9 |
| 5,885,211 A | 3/1999 | Eppstein et al. | |
| 6,022,316 A | 2/2000 | Eppstein et al. | |
| 6,027,496 A | 2/2000 | Loomis et al. | |
| 6,254,253 B1 * | 7/2001 | Daum et al. | 362/259 |
| 6,361,188 B1 * | 3/2002 | Kuts | 362/259 |
| 6,485,163 B1 * | 11/2002 | Hanchett | 362/259 |
| 6,517,221 B1 * | 2/2003 | Xie | 362/259 |

FOREIGN PATENT DOCUMENTS

| | | |
|---|---|---|
| WO | WO 97/22384 A | 6/1997 |
| WO | WO 98/33444 A | 8/1998 |
| WO | WO 98/51235 A | 11/1998 |

* cited by examiner

LIGHT BEAM GENERATION, AND FOCUSING AND REDIRECTING DEVICE

CROSS REFERENCE TO RELATED APPLICATIONS

The present application is a 35 U.S.C. § 371 national phase application from, and claims priority to, international application PCT/US00/16576, filed Jun. 15, 2000 (published under PCT Article 21(2) in English), which claims priority to U.S. Provisional Application No. 60/165,814, filed Nov. 16, 1999 and U.S. Provisional Application No. 60/140,003, filed Jun. 18, 1999, which applications are hereby incorporated herein in their entirety.

FIELD OF THE INVENTION

The invention relates in general to light beam generation and focusing devices, such as laser porators. More particularly, the invention relates to an improved light beam generation and focusing device adapted to emit at least one focused beam of light directed to at least two spaced locations on a surface plane.

BACKGROUND OF THE INVENTION

The use of laser porators for forming micropores in the stratum corneum has proven to be an important advancement in the healthcare field. Laser thermal ablation devices, such as that described in U.S. Pat. No. 5,885,211, provide a means of quickly and efficiently forming a micropore in the stratum corneum so that interstitial fluids can be easily gathered therefrom for testing the analytes present in the fluid. This has proven to be a very simple yet effective way of testing for glucose, for example. Moreover, the use of laser porators of the type described in the above-referenced patent has led to the development of improved glucose monitoring and testing systems, such as those developed by SpectRx, Inc. of Norcross, Ga.

When used as a porator for forming micropores in the stratum corneum of a person's skin, the known types of laser ablation devices emit and focus a beam of light at a focal point on the stratum corneum for defining, i.e. burning, an opening in the skin layer without penetrating any deeper into the epidermis of the person being tested. Thereafter, interstitial fluids will flow into the opening, or can be drawn into the opening by the use of a separate device, for example, the electro-poration device described in U.S. Pat. No. 6,022,316.

Additional laser ablation devices are described in U.S. Pat. No. 5,643,252, and in U.S. Pat. No. 6,027,496.

Figure 1:
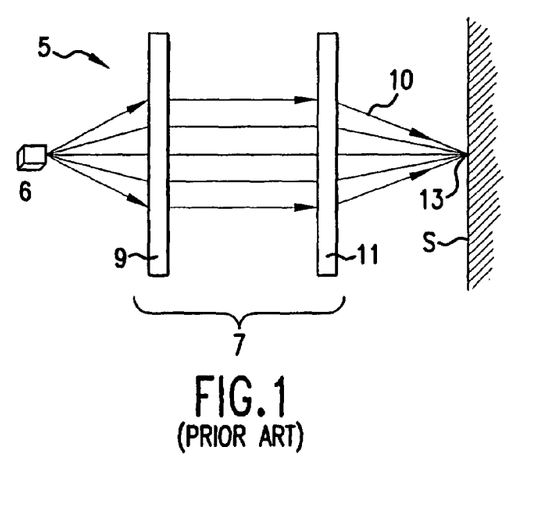
FIG. 1 is a schematic illustration of a known type of laser poration device.

What is common to the laser porators of the aforementioned patents, and as illustrated in FIG. 1 hereof, is a laser poration device 5 provided with a light source 6, typically a laser of some type, which laser emits a beam of light directed toward a collimating lens 9. The collimating lens gathers the beam of light and forms it into a columnar beam of light, and directs the beam of light to a spaced focusing lens 11. From the focusing lens, the beam of light is directed toward and focused on a focal point 13 defined on a spaced surface plane.

U.S. Pat. No. 5,643,252 illustrates a laser ablation device of the known type in FIGS. 1 and 3 thereof, and also shows in FIG. 5A thereof an ablation device having a spaced arrangement of prisms positioned with respect to the light source for use in splitting the beam of light emitted from the light source into separate beams of light, each beam of light being simultaneously directed to a surface plane. The device of the '252 patent also discloses, in FIG. 5B, a powered acousto-optic modulator for use in creating separate beams of light.

A problem with the known types of laser ablation/poration devices, however, results from the size of the device necessary to emit and focus a beam of light, and the need or desire to form more than one micropore in the stratum corneum of a person being tested.

There is a need, therefore, for a portable laser poration device which can quickly and easily emit at least one focused beam of light directed to at least two spaced focal points on a surface plane spaced from the device. Moreover, there is a need for such an improved device which remains relatively compact, yet flexible enough for use in a variety of applications. There is also a need for an improved laser porator which will more efficiently gather the beam of light emitted from the light source, focus the beam of light, and direct it to the at least two spaced locations on the surface plane.

SUMMARY OF THE INVENTION

The present invention provides an improved light beam generation and focusing device adapted for use in emitting and directing at least one focused beam of light to at least two spaced locations on a surface plane, which may include the stratum corneum of a person, and which overcome some of the design deficiencies of the known art. The light beam generation and focusing device of this invention provides a simple and efficient device which allows for a greater degree of flexibility in use when compared to the known types of laser porators. Moreover, the relative simplicity of the device of this invention, when contrasted with the known laser porators, addresses the problems of efficiently and cost effectively focusing at least one beam of light on a surface plane for defining an opening therein, and more preferably for defining an opening in at least two spaced locations therein.

The invention attains this degree of flexibility, as well as simplicity in design and construction, by providing an improved light beam generation and focusing device having a light source constructed and arranged to emit at least one beam of light, a lens assembly constructed and arranged to focus the at least one beam of light on the surface plane, and which is also constructed and arranged to direct the at least one beam of light to at least two spaced locations on the surface plane.

The lens assembly of the device comprises a collimating lens positioned with respect to the at least one beam of light, and a focusing lens spaced therefrom. The collimating lens may comprise a micro-lens, and more particularly may comprise a cylindrical micro-lens mounted directly to the light source. The light source may comprise a laser diode, and may further comprise a single active element laser diode chip, or multiple active element laser diode chips.

The device may also include, in one embodiment, a beam steering device constructed and arranged to direct the at least one beam of light to the at least two spaced locations on the surface plane. The beam steering device includes a beam steering optical element, and a drive motor, or drive motors, for moving the optical element so as to direct the at least one beam of light from a first location on the surface plane to a spaced second location thereon. The drive motor(s) may comprise a stepper motor, or other motors designed to function similarly.

The beam steering optical element may comprise a wedge prism or a tilted or angled plane in a first embodiment, each of which is driven by the drive motor. The optical element may also comprise a holographic or a diffractive optical imaging element in a second embodiment thereof such that a motor is not required, the optical element serving both to split the optical energy, i.e. the at least one beam of light, and to direct the at least one beam of light to the at least two spaced locations on the surface plane.

In another embodiment of the invention, the light beam generation and focusing device will be sized and shaped to fit within the hand of the device user, and will comprise a power supply, a light source, and a beam steering device fitted within the housing for directing the at least one beam of light emitted therefrom to the at least two spaced locations on the surface plane, or alternately may comprise at least two separate light sources within the housing, i.e., two separate laser diodes, used to emit separate beams of light.

Accordingly, in still another embodiment of the invention, the light source will comprise at least two laser diodes mounted on a common mounting block. Each of the laser diodes will preferably comprise a laser diode chip, although other types of suitable light emitting sources may be used. Each laser diode chip will be spaced approximately eight hundred (800) microns apart from each adjacent one of the laser diode chips for forming a predetermined pattern of light beams directed toward the surface plane.

The device also includes a controller/microprocessor coupled to the light source and/or to the beam steering device, where one is provided, for controlling the emission of the at least one beam of light, and for directing the at least one beam of light to the at least two spaced locations on the surface plane.

An improved method of emitting a focused beam of light directed to a surface plane results from the unique construction of this invention, the method including the steps of emitting at least one beam of light from a light source, passing the at least one beam of light through a lens assembly for being focused on the surface plane, and sequentially directing the at least one beam of light to at least two spaced locations on the surface plane with the device.

The step of sequentially directing the at least one beam of light may include the step using a beam steering device, or using at least two spaced light sources. Moreover, the method may include the step of sequentially directing the at least one beam of light to at least four spaced locations on the surface plane for forming a predetermined pattern thereon.

The objects, features, and advantages of the present invention will become apparent upon reading the specification, when taken in conjunction with the accompanying drawings, to which the invention is directed.

DETAILED DESCRIPTION OF THE INVENTION

Figure 2:
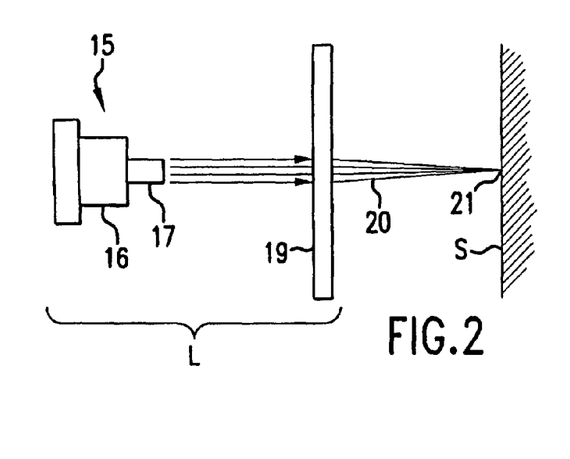
FIG. 2 is a schematic illustration of a first embodiment of the light beam generation and focusing device of this invention.
Figure 5:
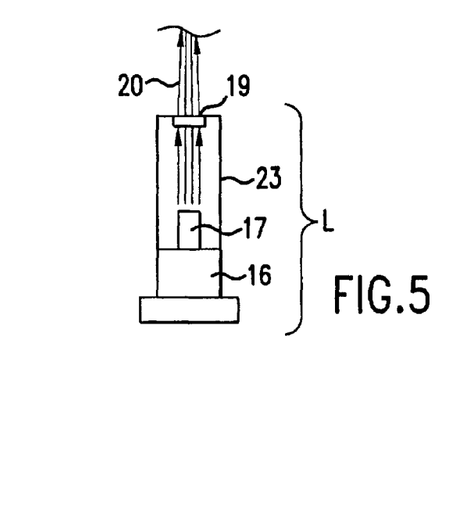
FIG. 5 is a schematic illustration of a combined light source and lens assembly for use with the light beam generation and focusing device of this invention.

Referring now in detail to the drawings, in which like reference characters indicate like parts throughout the several views, a first embodiment of the light beam generation and focusing device of 15 of this invention is illustrated in FIGS. 2 and 5. The device 15 is provided with a light source 16, here a suitable laser diode, for example those laser diodes manufactured by High Power Devices, or other laser diodes, also referred to as semiconductor diode lasers.

The light source 16 will preferably be a low-cost solid state laser diode capable of delivering a beam a light having an emission wave length of approximately eight hundred nanometers, or at such other wave lengths and power levels necessary for the intended purposes, which may include, but are not limited to, the forming of a micropore in the stratum corneum of a person's skin. Also, it is anticipated that the laser diode will be sized such that it will be sufficiently small so as to be portable enough to fit within a hand-held housing. Although not shown in FIGS. 2 and 5, the light source 16 will be powered by a suitable power source 25, which may include batteries, including, but not limited to, lithium, lithium-ion, nickel-metal hydride, and nickel-cadmium batteries; a capacatively charged power source, for example a storage capacitor; or a regulated wall type power supply capable of converting an electrical line voltage into the voltage needed to operate the device.

As shown in FIGS. 2–5, the light source 16 is fitted with a collimating lens 17 mounted directly to the light source. It is envisioned that the collimating lens 17 will comprise a micro lens, and may also therefore include a cylindrical micro-lens adapted to gather the light emitted from the light source 16, and to collimate the light so that it is emitted therefrom as an aligned and oriented beam of light directed toward a spaced focusing lens 19. The focusing lens will direct the beam of light toward a focal point 21 defined on a spaced surface plane "S", which is any desired surface plane, to include the stratum corneum of a person, or any other surface on which the beam of light is to be focused.

FIG. 5 illustrates an alternate embodiment of the arrangement of the device 15 shown in FIG. 2, in that the focusing lens 19 is affixed to a casing 23, the casing in turn being affixed to the light source 16 along with the collimating lens 17 so that the light source and lens assembly are formed as one compact assembly designated by the reference character "L." The construction shown in FIG. 5 offers a compact and efficient arrangement which is advantageous for use in a hand-held light beam generation and focusing device.

Figure 3A:
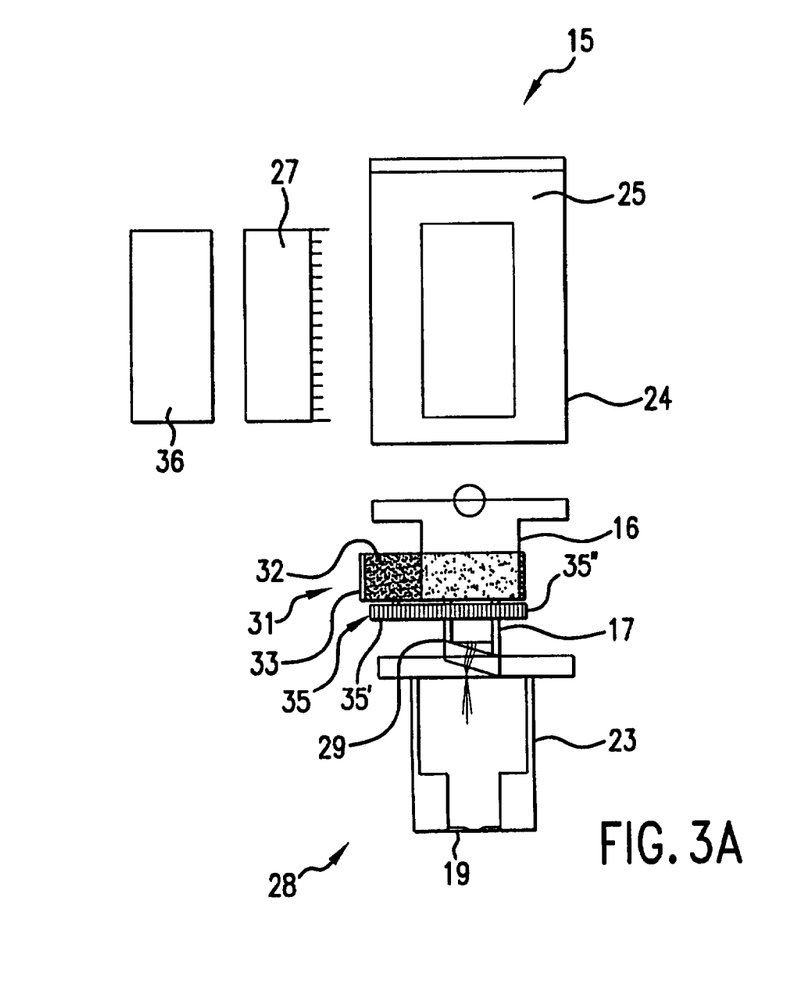
FIGS. 3A and 3B are schematic illustrations of a second embodiment of the light beam generation and focusing device of this invention.
Figure 3B:
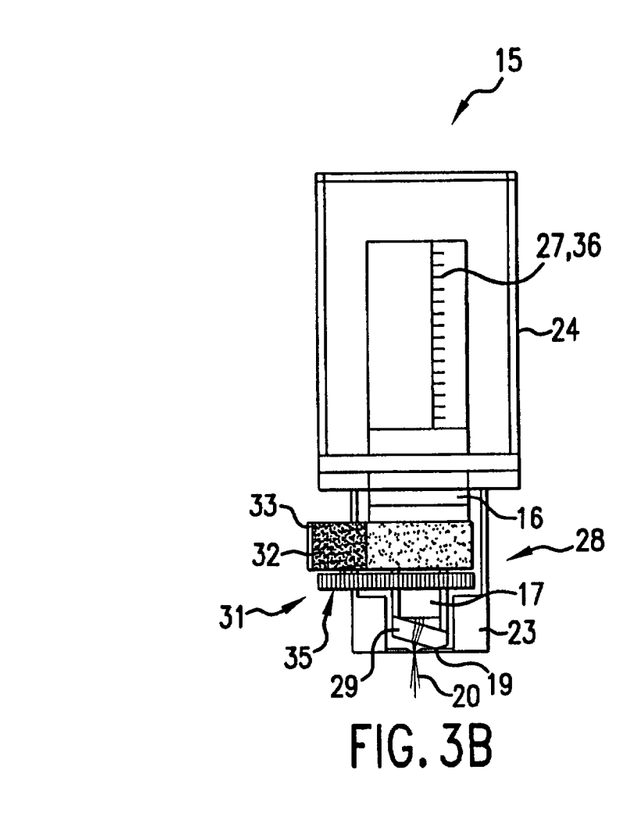
Figure 4:
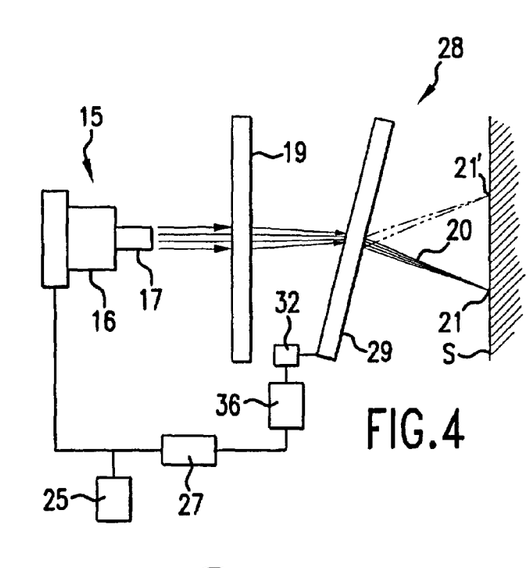
FIG. 4 is a schematic illustration of the light beam generation and focusing device of FIGS. 3A and 3B.

A second embodiment of the light beam generation and focusing device 15 is illustrated in FIGS. 3A & B, and in FIG. 4. In this embodiment of the device the light source 16 is again provided with a collimating lens 17, a micro-lens, fitted directly to the light source, with a spaced focusing lens 19 for focusing the beam of light 20. However, and unlike the first embodiment of this invention, the device 15 includes a beam steering device 28 constructed and arranged to receive the focused beam of light, and to direct the beam of light to at least two spaced locations on the surface plane. This is accomplished by positioning a beam steering optical element 29 between the focusing lens 19 and the surface plane S, such that the beam steering optical element intercepts the focused beam of light, and selectively directs the beam of light to a first focal point 21 on the surface plane, and then to at least a second spaced focal point 21' on the surface plane, shown in broken lines.

The beam steering device will include in a first embodiment thereof a drive assembly 31, best shown in FIGS. 3A and 3B, comprised of a drive motor 32, here a stepper motor, a mounting collar 33 for mounting the stepper motor to the casing 23 of the light source 16, a gear train 35 having a drive gear 35' rotated by the stepper motor 32, a driven gear 35" affixed to the beam steering optical element 29, and a motor controller 36 for operating the stepper motor so that it will move the beam of light 20 from the first focal point 21 to at least the second spaced focal point 21', as shown in FIG. 4. Although not shown, it is envisioned that more than one drive motor may be provided as a part of the beam steering device.

Referring now to FIGS. 3A and 3B, the light beam generation and focusing device 15 includes a hand-held housing 24 in which the device is fitted. The housing is sized and shaped to fit within the hand of the device user, and is provided with a suitable power supply 25, as described above. It is preferred, although not required, that the power supply be battery powered, and more preferably, that it be one of the known types of rechargeable batteries.

As shown in FIGS. 3A and 3B, the device 15 will include the compact collimating lens assembly shown in FIG. 5, which assembly will have the beam steering device 28 fitted thereto by the mounting collar 33 as described above. A controller 27, also referred to herein interchangeably as a microprocessor or microcontroller, is provided as a part of the device, and is positioned within the housing 24 for controlling the light source such that a pulsed laser beam is generated and emitted therefrom, and which also signals a motor controller 36 for controlling the operation of the beam steering device drive motor.

The construction of the controller 27 and of the motor controller 36 is not shown in greater detail as these are otherwise conventional control or microprocessor chips adapted for use in both controlling the operation of the light source 16, as well as operating the motor 32. Each of the controller 27 and the motor controller 36, as well as the controller 64 described hereinbelow, therefore comprises a conventional microprocessor available from a variety of vendors/manufacturers in known constructions, and which will either be pre-programmed or programmable, as known, and will also be provided with a memory or access to a memory storage and retrieval device.

Moreover, although a stepper motor 32 is disclosed herein for use in driving the beam steering optical element 29, it is understood by those skilled in the art that any suitable motor, or controllable actuator, including, but not limited to a servomotor, a solenoid, a pneumatic cylinder, a hydraulic cylinder, or the like, could be used for this purpose, as desired. A stepper motor is preferred here for its ability to precisely control the movement of the beam steering device.

The actual physical construction of the device 15 shown in FIGS. 3A and 3B is not discussed in greater detail for the reason that the manner and method of assembling the components is well known, and will comprise the use of a PC board to which the controllers 27 and/or 36 will be affixed, and to which the power supply 25 will also be connected through the known types of electronic circuits, as is the light source 16.

Although, the device 15 shown in FIGS. 3A and 3B uses the compact light source and lens assembly L shown in FIG. 5, it is also envisioned that the device could use conventional spaced collimating and focusing lenses which are not affixed to or mounted on the light source 16 and the casing 23, respectively, as shown, for example, in U.S. Pat. No. 5,885,211 to Eppstein et al., the provisions of which are incorporated fully herein by this reference.

Figure 6A:
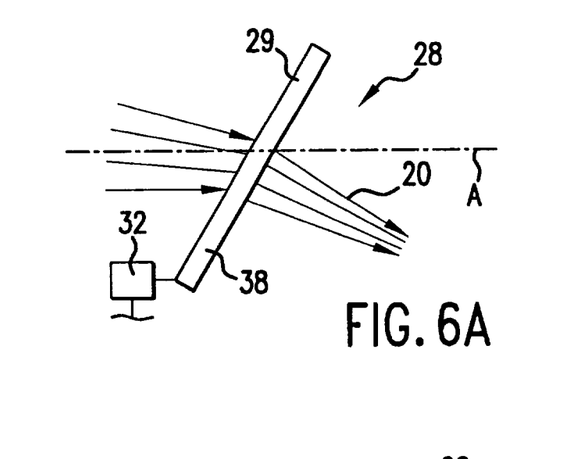
FIGS. 6A–6C illustrates three separate embodiments of a beam steering optical element that may be used as a part of the beam steering device of the invention.
Figure 6B:
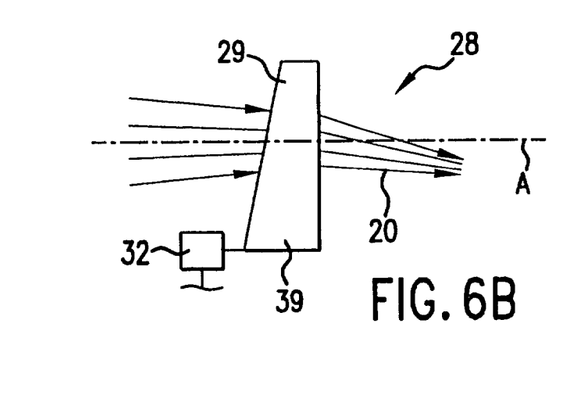
Figure 6C:
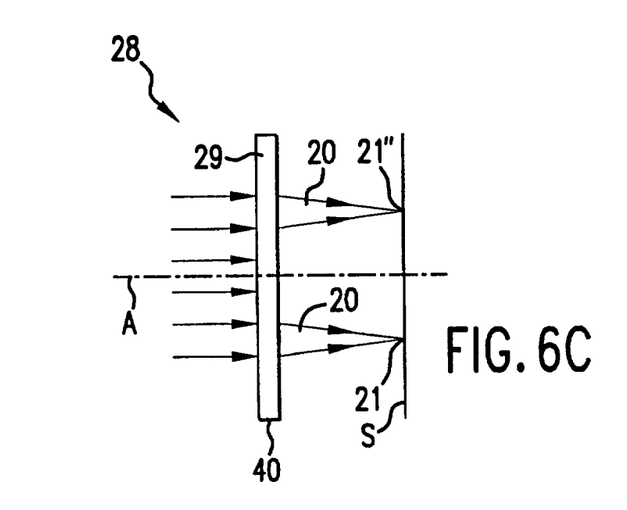

Moreover, although the beam steering optical element 29 shown in FIG. 4, as well as in FIG. 6A is an inclined optical plane 38, it is anticipated that other embodiments of the beam steering optical element may be used, as shown in FIGS. 6B and 6C. Referring now to FIG. 6B, the beam steering optical element 29 may comprise a wedge shaped prism 39 positioned anywhere in the optical beam path, but which is preferably positioned between the focusing lens (not shown) and the focal point 21 on the surface plane (FIG. 4). The prism 39 will be moved by the drive motor 32, the prism being held by a suitable support structure or framework with respect to the light source 16 of FIGS. 2–5. Both the optical plane and the prism will be rotated about a central axis "A" positioned coaxially with the axis of the light source for directing the beam of light to the at least two spaced locations 21, 21', on the surface plane.

The optical plane 38 comprises a tilting, flat optical window, or plate, which may be positioned between either the light source and the collimating lens, or between the focusing lens and the surface plane. The focal point of the beam of light can thereby be steered by tilting this flat optical window in the x and y dimensional planes, where the thickness of the window affects the beam of light via refraction of the light beam leading to a lateral translation of the focal point in an amount related to the degree of tilt in the desired direction. The steering of the beam of light in this fashion offers some cost advantages over an optical wedge in that an optical window/plane is a simpler element to fabricate.

Each of the optical plane 38 of FIGS. 4 and 6A, and the prism 39 of FIG. 6B comprise an optical quality glass or plastic element, respectively, the plane 38 being a plate or sheet of glass or plastic, whereas the prism 39 will shaped as a prism of any suitable construction or configuration. All that is required is that the plane 38, prism 39 be suitable for bending light to be incident at the required distance from the optical axis, and be provided with suitable transmissability and anti-reflective coatings at the desired wavelengths. The optical plane of FIGS. 4 and 6A is mounted in an inclined fashion in a holder, while the prism is mounted in an erect manner.

Yet another embodiment of the beam steering device 28 is shown in FIG. 6C, which embodiment does not utilize the drive assembly 31 of FIGS. 3A and 3B. Instead, a holographic or diffractive optical element 40 is used which masks the beam of light received from the upstream light source, such that discrete beams of light 20 are passed toward the surface plane to the separate focal points 21, 21" thereon. This type of holographic or diffractive imaging into multiple focal points is preferably done using a monochromatic light source, such as a laser diode. Additionally, when using these types of holographic or diffractive optical elements, to ensure an equal distribution of optical energy to the various focal points, it is preferable to mask the first order image and use only the multiple second order images emitted from the element.

Although, reference has been made hereinabove to a first focal point 21 and a second focal point 21', or 21", respectively, it is envisioned that the beam steering embodiments of the device 15 will be used to direct the beam of light to at least two, and as many more spaced locations/focal points on the surface plane as desired. A preferred light pattern here is shown as having four spaced focal points on the surface plane spaced at least eight hundred microns apart from one another for defining a predetermined pattern of focal points, or openings if the device is being used to define a plurality of micropores through the stratum corneum and into the viable layers of the epidermis of a person. The beams of light emitted from the device, in each of its several embodiments, will preferably penetrate to a depth of at least 80 to 100 microns beneath the outermost surface of the skin layers. This type of construction is desirable for allowing the interstitial fluids to be collected from a plurality of closely grouped micropores for expediently testing the interstitial fluids for analytes or for any other desired purpose(s).

It is envisioned, therefore, that the beam(s) of light can be formed into any type of geographic pattern capable of being defined on a surface plane, which may thus include a hexagonal shaped pattern, a rectangular pattern, a circular pattern, or a pattern of any desired type, based upon the operating program stored within the controller 27 and/or the motor controller 36 of the device, all as desired by the end user of the device, based on the known types of programmable control/microprocessor chips available in the art, and the known methods of programming same.

Figure 7:
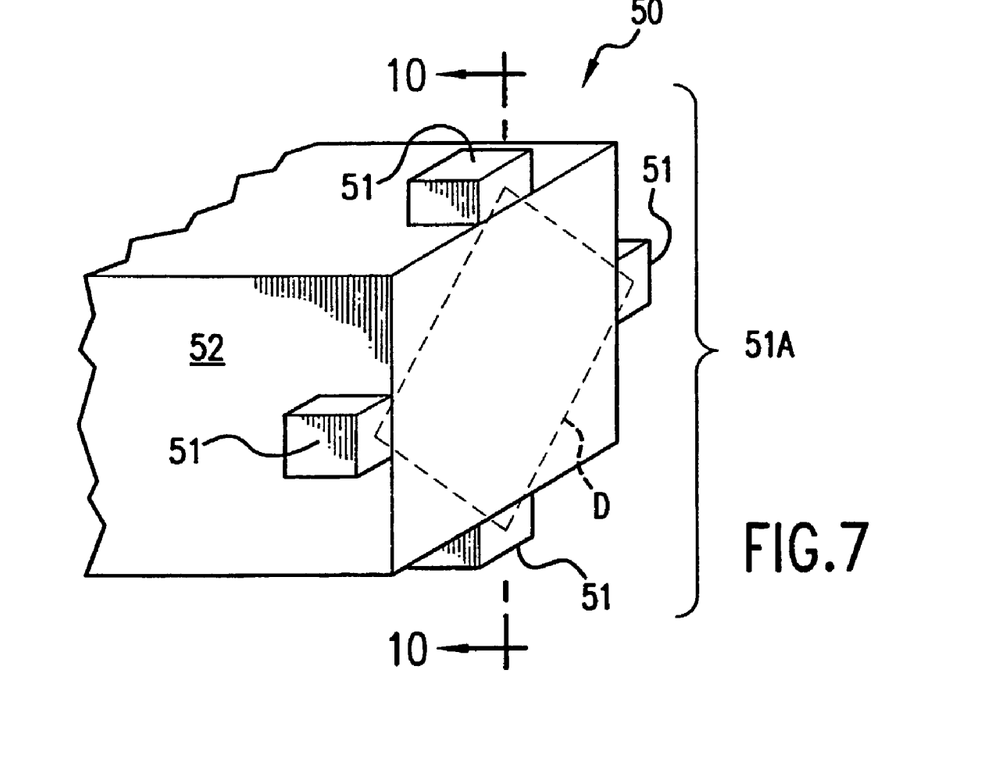
FIG. 7 is a partial schematic perspective illustration of a third embodiment of the light beam generation and focusing device of this invention.
Figure 8:
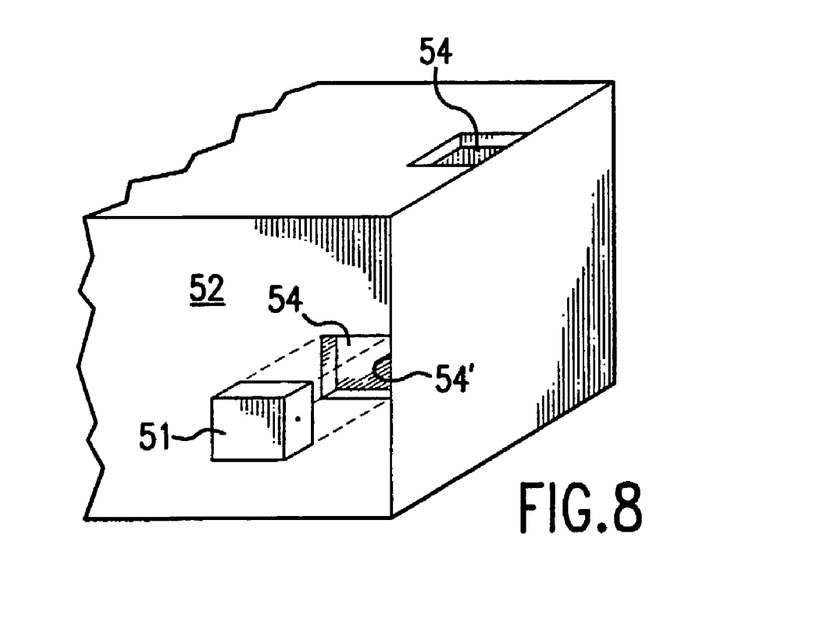
FIG. 8 is a partial exploded schematic view of the embodiment of the light beam generation and focusing device of FIG. 7.
Figure 9:
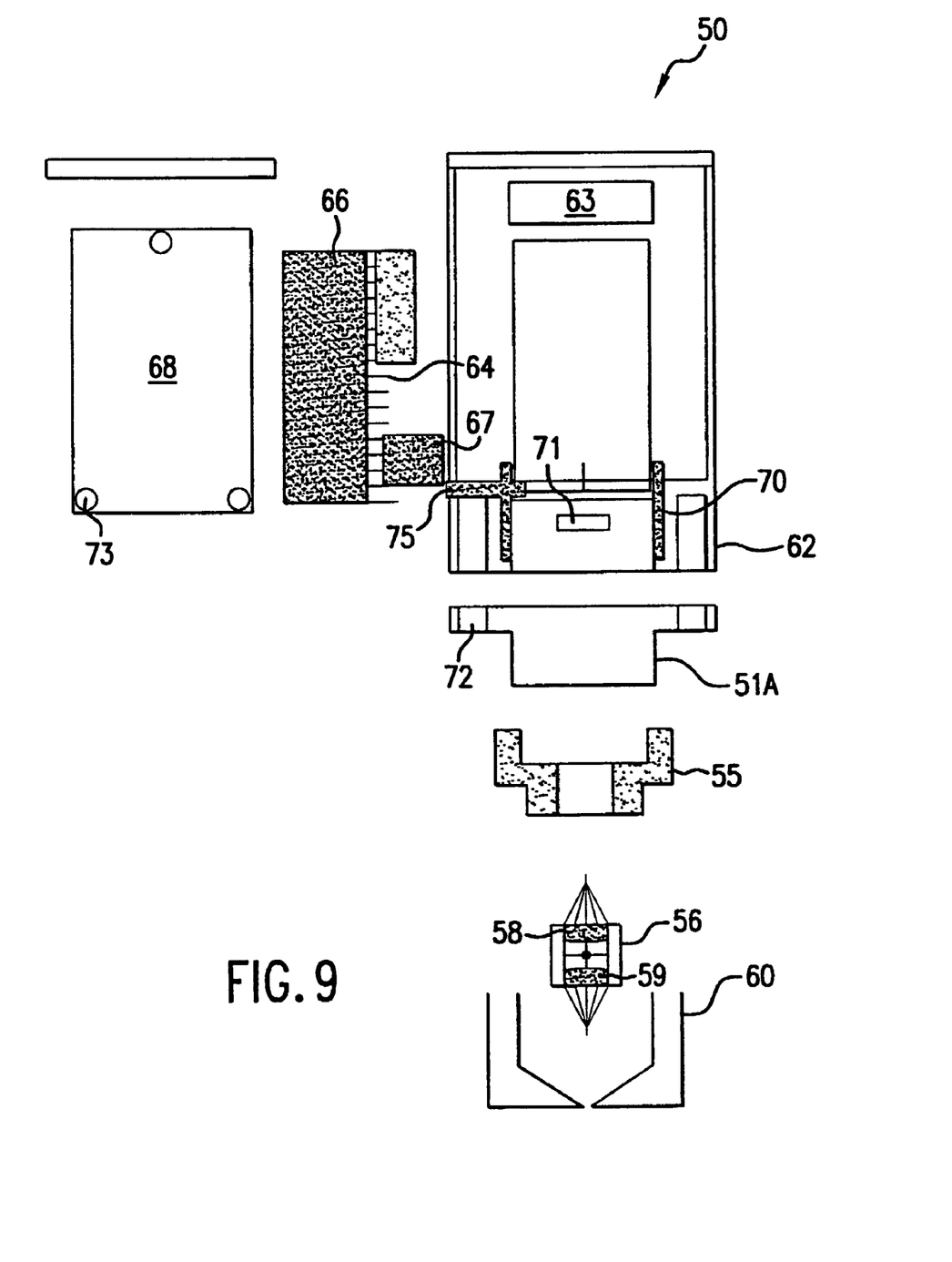
FIG. 9 is a schematic illustration of the light beam generation and focusing device of FIGS. 7 and 8.

A fourth embodiment of the light beam generation and focusing device 50 is illustrated in FIGS. 7–9. Referring first to FIGS. 7 and 8, in this embodiment of the invention, rather than using a beam steering device 28 as shown in FIGS. 3A–4, a plurality of light sources 51, again laser diodes as described above, are mounted to a common mounting block 52 in the desired geometric pattern to be defined on the surface plane of FIGS. 10–12. Each one of the light sources 51 will be mounted on the mounting block, which also functions as either a ground or an electrode, by an insulated wire bonding pad 54 for forming either the anodic or cathodic lead for the laser diode, respectively, whereas the respective cathodic/anodic leads will be formed through the known wire bonding techniques. The emitting facets of the respective laser diodes will preferably be aligned along the "z" dimensional axis such that when collimated and re-imaged to focus on the surface plane, the focal point of each individual laser diode will lie on the common surface plane.

Each of the insulated wire bonding pads 54 will be separately positioned within a respective one of the depressions 54' defined within the mounting block, with the laser diodes being soldered or otherwise bonded to the heatsink and wired to the bonding pads, and thus to the mounting block 52. The wire bonding pads are insulated from the mounting block so that the block can provide the "opposite" electrical supply, be it positive, or negative, as desired. The mounting block, be it a common ground or a common positive, will preferably comprise a block of high thermal conductivity copper, or other high quality thermally conductive heatsink materials.

Four spaced light sources 51, illustrated in FIG. 7 as four separate laser diodes, together define a predetermined pattern shown by the broken lines as designated by the reference character "D". Each of the respective laser diodes will be spaced approximately eight hundred microns apart from each adjacent laser diode within this predetermined pattern. Here, rather than emitting a single beam of light with a single light source and then "steering" the beam of light, a plurality of separate light beams, in this instance four light beams, will be emitted from the device in sequential fashion toward the surface plane S. This eliminates, entirely, the need for any kind of mechanical device interposed between the respective light sources 51 and the surface plane. As with the beam steering embodiment of the invention, the beams of light emitted from the respective light sources are capable of being formed into any type of geographic pattern capable of being defined on a surface plane, as governed by the mounting pattern of the laser diodes on the mounting block.

Referring now to FIG. 9, the construction of the light beam generation and focusing device 50 is described in greater detail. The device 50 is provided with four light sources 51, each of which comprises a laser diode, for example a single active element laser diode chip. Each laser diode is affixed to the mounting block 52 as an assembly 51A. The assembly fits within a lens holder 55, to which a lens assembly 56 is fitted. The lens assembly 56, as shown in FIG. 9, includes a collimating lens 58 and a spaced focusing lens 59. A casing 60 is fit over the lens assembly 56, and hold the lens assembly in position with respect to the lens holder 55 and the laser diode assembly 51A.

The casing 60, lens assembly 56, and laser diode assembly 51A are fitted within a housing 62, the housing being sized and shaped to be held within the hand of a user. A suitable power supply 63 is provided within the housing, this being the same type of power supply as is power supply 25, described above.

The device 50 will include a controller/microcontroller 64, a known type of microprocessor, as described hereinabove, and is provided with a resistor pin network 66 which provides a series of pull down resistors used to prevent the lasers from firing without the proper actuating command. The device 50 also includes a three pin header 67, provided as a programming port for the controller 64, in known fashion. The controller 64, as well as the resistor network 66, and the header 67 are fit within an electronics compartment defined within the housing, with an electronics compartment cover 68 fitted thereto for enclosing the electronics controls of the device within the housing.

Still referring to FIG. 9, a plurality of spaced pogo pins 70 are provided for connection to the power supply 63, assuming the power supply comprises batteries, as described hereinabove, batteries being preferred for providing ease of portability in the use of the device. The housing is also provided with a power switch 71 for operating the device, and includes a plurality of conventional fasteners 72 for affixing the laser diode assembly 51A to the housing, and a plurality of fasteners 74 for affixing the electronics compartment cover to the housing as well. The device 50 is also provided with a bi-color LED 75 for the purpose of indicating a ready status in which the device is charged and ready for use, and a firing status indicating that the light source, the laser diode or diodes, are firing. For example, a flashing green light may be used to indicate the ready status, and a flashing red or amber light to indicate that the device is firing, and to meet the appropriate BRH/FDA laser safety warning requirements.

Figure 10:
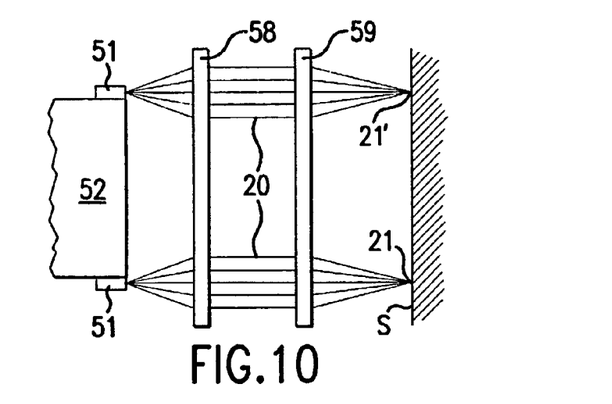
FIG. 10 is a schematic side elevational view along line 10—10 of FIG. 7.

Referring now to FIG. 10, the embodiment of the device shown in FIGS. 7–9 is shown in a schematic side elevational view. Two spaced light sources 51, a pair of laser diodes, are shown affixed to the mounting block 52. Each light source emits a separate beam of light 20 toward a first collimating lens 58, which gathers and collimates the light, and passes it to a spaced downstream focusing lens 59, such that the beams of light are separately focused at focal points 21, 21' on the surface plane. Again, although only two focal points are shown, it is understood by reference to FIGS. 7 and 8, that there will be at least four such focal points formed into the shape of a predetermined pattern on the surface plane.

Figure 11:
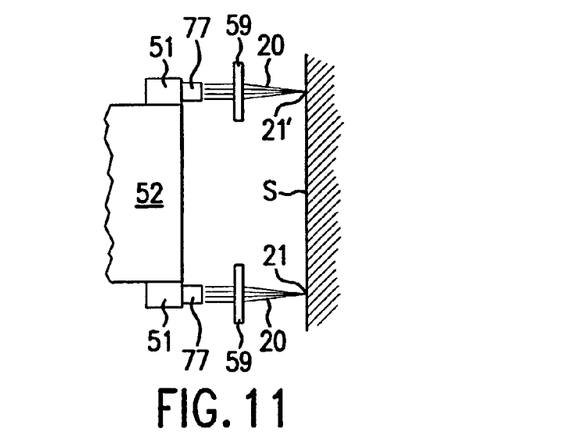
FIG. 11 is a schematic illustration of a fourth embodiment of the light beam generation and focusing device of this invention.

The device of FIG. 10 may be used with any conventional lens assembly, such as that shown in FIG. 9, and comprising lens assembly 56. However, the embodiment of light beam generation and focusing device 50 shown in FIGS. 7–10 may also be used with the micro-lens construction of the device shown in FIGS. 2–5, such that, and as shown in FIG. 11, a micro-lens 77 is affixed to each light source/laser diode 51 for gathering and collimating the respective light beams, and passing the light beams to a spaced focusing lens 59, which then passes the light beams to two separate focal points 21, 21'.

Figure 12:
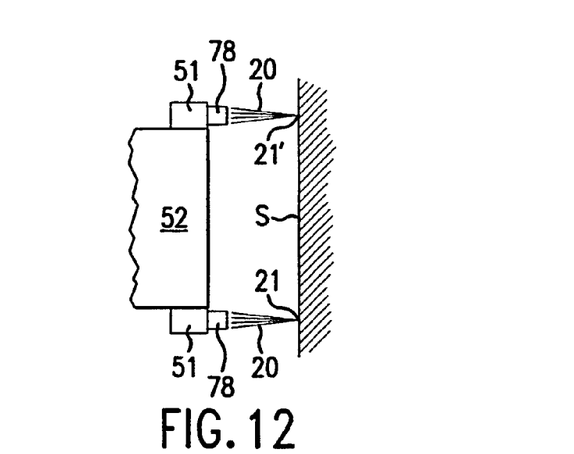
FIG. 12 is a schematic illustration of a fifth embodiment of the light beam generation and focusing device of this invention.

If full advantage of the construction shown in FIGS. 2–5 is to be achieved, then the construction of FIG. 12 results, in which each one of the light sources 51 is provided with a compact lens assembly and casing as shown in FIG. 5, such that the micro-lens is affixed directly to the laser diode, and a casing is also affixed to the laser diode, whereupon the focusing lens is affixed to the casing so that no separate collimating and focusing lens assemblies are needed for focusing and directing the separate beams of light 20 towards the focal points 20, 21' on the surface plane.

In the embodiment of the light beam generation and focusing device shown in FIGS. 2–6, the construction of the device, namely there being a beam steering device 28 provided as a part thereof, results in the sequential direction of a focused beam of light to at least two, and more preferably four, spaced focal points 21 on the surface plane. In particular, for the embodiments of the device shown in FIGS. 6A and 6B, a stepper motor and a focal plane 38 and/or a prism 39 are used to steer the beam of light. As it necessary to physically move the beam steering optical element 29 for directing the beam of light 20 to any separate one of the different focal points 21, 21', and so on defined on the surface plane, the direction of the beam of light must necessarily be done in sequence with a first focal point being established, and with any and all subsequent focal points being established in sequential order.

For the embodiment of the device 15 shown in FIG. 6C, using the holographic or diffractive optical element 40, and which does not otherwise use a drive motor as a part of the beam steering device, it is possible that the beam of light may be simultaneously directed to the several focal points formed on the surface plane. If, however, and not illustrated but envisioned, the holographic/diffractive element is used in combination with a beam steering device positioned between the light source 16 and the downstream holographic plate, then the focal points would be established sequentially, all as desired, and as programmed into the controller 27 of the device.

With regard to the embodiment of the device illustrated in FIGS. 7–12, however, still greater flexibility results from the construction of the device in that the controller 64 will preferably operate each of the four light sources/laser diodes 51 sequentially for emitting separate beams of light from each respective laser diode toward the surface plane. However, due to the construction of the device shown in FIGS. 7–12, it is also possible that the controller 64 could be programmed so that each one of the light sources 51 fires simultaneously, although this is not preferred when compared to sequential operation of the device in that the peak power drain on the battery of the device would be much greater than from sequential operation. Also it is possible that if all of the laser diodes of the device were operated simultaneously the device would heat up more quickly, requiring a greater cooling capacity for the mounting block 52, and there would likely be a noticeable discomfort factor for the person on whose stratum corneum, for example, the multiple light beams were focused as the surface plane.

Figure 13:
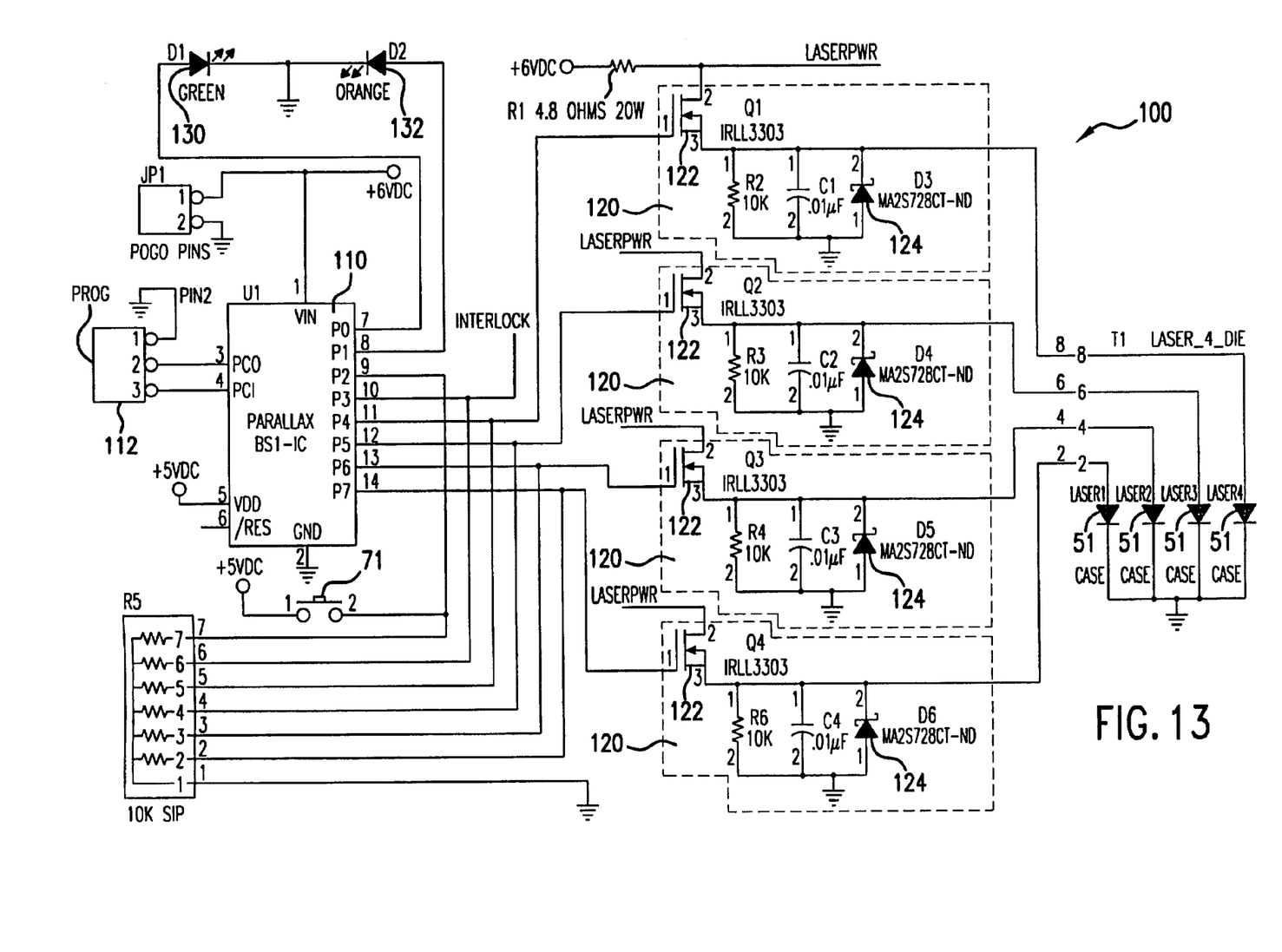
FIG. 13 is a circuit diagram of the control circuit used in connection with the embodiments of the light beam generation and focusing device of FIGS. 2–12.

Referring to FIG. 13, a control circuit 100 is shown which may be used to operate either the stepper motor for the beam steering device 28 (FIGS. 3A–4, 6A–6B) or to drive the multiple lasers in the embodiment shown in FIGS. 7–12. The control circuit 100 comprises a programmable controller 110, the power switch 71 (referred to above), and a plurality of laser drive circuits 120. In addition, the circuit 100 drives status indicators 130 and 132 (referred to above) which are, for example, the bi-colored light emitting diodes (LEDs) 75. Each laser drive circuit 120 comprises a field effect transistor (FET) 122 that act as a high current switch to activate a corresponding one of the light sources 51. The light sources 51 are, for example, laser diodes. A diode 124 is included in each laser drive circuit 120 to provide protection for the light sources 51 in the event a static discharge occurs. The parallel resistor-capacitor combination in each laser drive circuit 120 acts as a filter for pulse smoothing and to reduce electrical switching spikes that may occur when the control circuit 100 is powered on.

The controller 110 is, for example, a programmable micro-controller and is programmed to time the on/off time signals coupled to the laser drive circuits 120 for sequencing the operation of the light sources 51. For example, four of the pins may be programmed to the proper sequence of time on vs. time off to drive the drive (stepper) motor for the beam steering device 28. Alternatively, four of the pins may be programmed to the proper sequence of time on vs. time off to power the field effect transistors which act as the high current switches used to turn the light source(s), here laser diodes, on and off in the desired sequence. The outputs of the controller 110 that is coupled to the laser drive circuits 120 are found at pins 11–14 thereof.

The signal on each of these pins is coupled to the gate of a FET 122 of a corresponding laser drive circuit 120, and causes the desired time on vs. time off for a light source. The controller 110 also drives the status indicators 130 and 132 according to the status of the signals on pins 11–14. Programming of the controller 110 is achieved by a suitable programming interface 112 that supplies programming signals to pins 3 and 4 of the controller 110.

The controller 110 is also programmable to generate similar timing signals at pins 11–14 to drive a stepper motor in the beam steering device 28 shown in FIGS. 3A–4, 6A–6B, thereby controlling the location of the laser beam.

Although, several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein, and that many modifications and other embodiments of the invention are intended to be included within the scope of the appended claims. Moreover, although specific terms are employed herein, as well as in the claims, they are used in the generic and descriptive sense only, and not for the purposes of limiting the described invention, nor the claims which follow.

We claim:

1. A light beam generation and focusing device for directing at least one focused beam of light at a target surface plane, said device comprising:
  a light source constructed and arranged to emit at least one beam of light; and
  a lens assembly constructed and arranged to focus said at least one beam of light on the surface plane;
  said device being constructed and arranged to sequentially direct the at least one beam of light to at least two spaced locations on the surface plane including at least one rotating wedge interposed in the path of said light beam capable of redirecting the beam to multiple locations and actuate said light beam when said wedge is in position to direct the beam to said target; said light source comprising at least two laser diodes mounted on a mounting block and wherein said mounting block includes at least two generally planar walls generally orthogonal to the target locations, and that the spacing between said walls generally fixed the relative spacing between the targets of the diodes.

2. The device of claim 1, comprising a microcontroller coupled to each said laser diode and adapted to sequentially operate each said laser diode with respect to one another for emitting said at least one beam of light and for sequentially directing said at least one beam of light to said at least two spaced locations on the surface plane.

3. The device of claim 1, said mounting block comprising a heat sink mounting block having a first planar surface, a spaced parallel second planar surface, and a plurality of sides adjoining one another and each said planar surface along their respective common edges.

4. The device of claim 3, each of said at least two laser diodes being mounted to a separate one of the sides of said mounting block.

5. The device of claim 3, comprising a separate insulated wire bonding pad on said mounting block for each respective one of said at least two laser diodes.

6. A light beam generation and focusing device for directing at least one focused beam of light at a target surface plane, said device comprising:
  a light source constructed and arranged to emit at least one beam of light; and
  a lens assembly constructed and arranged to focus said at least one beam of light on the surface plane;
  said device being constructed and arranged to sequentially direct the at least one beam of light to at least two spaced locations on the surface plane including at least one rotating wedge interposed in the path of said light beam capable of redirecting the beam to multiple locations and actuate said light beam when said wedge is in position to direct the beam to said target; said light source comprising at least two laser diodes mounted on a mounting block and wherein said mounting block includes at least two generally planar walls generally orthogonal to the target locations, and that the spacing between said walls generally fixed the relative spacing between the targets of the diodes and wherein each of said at least two laser diodes comprising a single active element laser diode chip; and wherein said light source comprising four spaced laser diodes mounted on a common mounting block and wherein said mounting block includes 4 generally planar walls for defining the relative spacing between said the targets of the diodes.

7. The device of claim 6, each said laser diode chip being spaced approximately eight hundred microns from each adjacent one of said laser diode chips.

8. The device of claim 6, said laser diode chips being spaced apart from one another to form a predetermined pattern of beams of light directed to the surface plane.

9. A light beam generation and focusing device capable of directing at least two separate unsplit focused beams of light at a surface plane, said device comprising:
  a light source constructed and arranged to emit at least one beam of light, said light source comprising at least two laser diodes mounted on a mounting block, said mounting block including a heat sink for cooling said diodes and for creating a fixed spacing therebetween comprising first and second spaced apart planar surfaces upon which said diodes are immovably attached,
  a lens assembly constructed and arranged to focus said at the beam of light from each diode on the surface plane; and
  said device being constructed and arranged to direct beams of light to at least two apart spaced locations on the surface plane.

10. A light beam generation and focusing device according to claim 9 wherein said mounting block has planar opposing walls and recesses for receiving at least a portion of each diode to actually align their position.

11. A light beam generator and focusing device according to claim 10 further including an insulating portion on said planar surfaces between said heat sink and said diodes.

12. A light beam generation and focusing device for directing at least one focused beam of light at a target surface plane, said device comprising:
  a light source constructed and arranged to emit at least one beam of light; and
  a lens assembly constructed and arranged to focus said at least one beam of light on the surface plane:
  said device being constructed and arranged to sequentially direct the at least one beam of light to at least two spaced locations on the surface plane including at least one rotating wedge interposed in the path of said light beam capable of redirecting the beam to multiple locations and actuate said light beam when said wedge is in position to direct the beam to said target, said device being constructed and arranged to sequentially direct the beam of light to at least four spaced locations on the surface plane in a predetermined pattern and wherein, each of the at least four spaced locations on the surface plane being spaced approximately eight hundred microns from each adjacent one of said at least four spaced locations thereon.

13. A light beam generation and focusing device for directing at least one focused beam of light at a target surface plane, said device comprising:
  a light source constructed and arranged to emit at least one beam of light; and a lens assembly constructed and arranged to focus said at least one beam of light on the surface plane;

said device being constructed and arranged to sequentially direct the at least one beam of light to at least two spaced locations on the surface plane including at least one rotating wedge interposed in the path of said light beam capable of redirecting the beam to multiple locations and actuate said light beam when said wedge is in position to direct the beam to said target; said light source and said lens assembly being fitted within a housing sized and shaped to fit in the hand of a device user and wherein, said light source comprising at least two laser diodes mounted to a mounting block positioned within said housing and wherein said mounting block includes at least two generally planar walls generally orthogonal to the target locations, and that the spacing between said walls generally fixed the relative spacing between targets of the diodes.

14. A light beam generation and focusing device for directing at least one focused beam of light at a target surface plane, said device comprising:

a light source constructed and arranged to emit at least one beam of light; and a lens assembly constructed and arranged to focus said at least one beam of light on the surface plane;

said device being constructed and arranged to sequentially direct the at least one beam of light to at least two spaced locations on the surface plane including at least one rotating wedge interposed in the path of said light beam capable of redirecting the beam to multiple locations and actuate said light beam when said wedge is in position to direct the beam to said target; said light source and said lens assembly being fitted within a housing sized and shaped to fit in the hand of a device user and said light source comprising at least two laser diodes mounted to a mounting block positioned within said housing and wherein said mounting block includes at least two generally planar walls generally orthogonal to the target locations, and that the spacing between said walls generally fixed the relative spacing between targets of the diodes and further comprising a controller coupled to each of said at least two laser diodes and adapted to sequentially operate each said laser diode with respect to the other for directing the beam of light to said at least two spaced locations on the surface plane.

15. A light beam generation and focusing device for directing at least one focused beam of light at a target surface plane, said device comprising:

a light source constructed and arranged to emit at least one beam of light; and a lens assembly constructed and arranged to focus said at least one beam of light on the surface plane;

said device being constructed and arranged to sequentially direct the at least one beam of light to at least two spaced locations on the surface plane including at least one rotating wedge interposed in the path of said light beam capable of redirecting the beam to multiple locations and actuate said light beam when said wedge is in position to direct the beam to said target; said light source comprising at least two laser diodes mounted on a mounting block and wherein said mounting block includes at least two generally planar walls generally orthogonal to the target locations, and that the spacing between said walls generally fixed the relative spacing between the targets of the diodes; said light source comprising four spaced laser diodes mounted on a common mounting block and wherein said mounting block includes 4 generally planar walls for defining the relative spacing between said the targets of the diodes.

16. A method of reliably generating focused light beams directed to a surface plane at a predetermined distance from each other, comprising:

a) fixing the location on multiple light beam sources on a rigid heat sinking material;

b) emitting at multiple light beams;

c) passing the beams of light through a lens assembly and focusing said at least one beam of light on the surface plane in response thereto; and d) sequentially directing each beam of light to a plurality of spaced locations on the surface plane, e) sequentially directing the at least one beam of light to at least four spaced locations on the surface plane in a predetermined pattern f) directing a beam of light to each of said at least two spaced locations on the surface plane so that each said location is spaced approximately eight hundred microns from each adjacent one of said spaced locations.

17. A light beam generation and focusing device for directing at least one focused beam of light at a surface plane, said device comprising:

a light source constructed and arranged to emit at least one beam of light, said light source comprising at least two laser diodes mounted on a mounting block, said mounting block comprising a copper mounting block having a first planar surface, a spaced parallel second planar surface, and a plurality of sides adjoining one another and each said planar surface along their respective common edges, said mounting block including a separate insulated wire bonding pad on said mounting block for each respective one of said at least two laser diodes; and a lens assembly constructed and arranged to focus said at least one beam of light on the surface plane;

said device being constructed and arranged to sequentially direct the at least one beam of light to at least two spaced locations on the surface plane.

* * * * *